US008838628B2

(12) United States Patent
Leighton et al.

(10) Patent No.: US 8,838,628 B2
(45) Date of Patent: Sep. 16, 2014

(54) INTELLIGENT SEARCH TOOL FOR ANSWERING CLINICAL QUERIES

(76) Inventors: Bonnie Berger Leighton, Newtonville, MA (US); Nathan P. Palmer, Somerville, MA (US); Patrick R. Schmid, Cambridge, MA (US); Isaac S. Kohane, Newton, MA (US)

( * ) Notice: Subject to any disclaimer, the term of this patent is extended or adjusted under 35 U.S.C. 154(b) by 0 days.

(21) Appl. No.: 12/766,866

(22) Filed: Apr. 24, 2010

(65) Prior Publication Data

US 2011/0047169 A1    Feb. 24, 2011

Related U.S. Application Data

(60) Provisional application No. 61/172,381, filed on Apr. 24, 2009.

(51) Int. Cl.
*G06F 17/30* (2006.01)
*G06F 19/00* (2011.01)

(52) U.S. Cl.
CPC ...... *G06F 17/30675* (2013.01); *G06F 19/3443* (2013.01)

USPC .......................................................... 707/756

(58) Field of Classification Search
None
See application file for complete search history.

(56) References Cited

U.S. PATENT DOCUMENTS

| 2003/0163597 A1* | 8/2003 | Hellman et al. ............... 709/316 |
| 2004/0063099 A1* | 4/2004 | Retieff ............................... 435/6 |
| 2004/0193593 A1* | 9/2004 | Sacco .................................. 707/3 |
| 2006/0074991 A1* | 4/2006 | Lussier et al. ................. 707/200 |
| 2006/0271556 A1* | 11/2006 | Mukherjee et al. ............. 707/10 |
| 2007/0130206 A1* | 6/2007 | Zhou et al. .................. 707/104.1 |
| 2007/0143273 A1* | 6/2007 | Knaus et al. ....................... 707/3 |
| 2007/0282824 A1* | 12/2007 | Ellingsworth ..................... 707/5 |
| 2009/0024615 A1* | 1/2009 | Pedro et al. ........................ 707/5 |
| 2011/0087670 A1* | 4/2011 | Jorstad et al. ................. 707/741 |

* cited by examiner

*Primary Examiner* — Bai D. Vu
(74) *Attorney, Agent, or Firm* — David H. Judson

(57) ABSTRACT

A scalable infrastructure for searching multiple disparate textual databases by mapping their contents onto a structured ontology, e.g., of medical concepts. This framework can be leveraged against any database where free-text attributes are used to describe the constituent records.

16 Claims, 2 Drawing Sheets

INTELLIGENT SEARCH TOOL FOR ANSWERING CLINICAL QUERIES

This application is based on and claims priority to Ser. No. 61/172,381, filed Apr. 24, 2010.

TECHNICAL FIELD

This application relates generally to information retrieval systems.

BACKGROUND OF THE INVENTION

Information retrieval systems are known in the art. Such systems generally offer users a variety of means of expressing user intentions through queries. These include text search, parametric search, structured queries, selection from alternatives (i.e., browsing or navigation), and range specification. In general, the systems offer users a means of expressing queries using either a structured language (e.g., a language like SQL) or an informal input mechanism (e.g., English keyword search). When the input mechanism is informal, the problems of ambiguity may arise from the language itself. But, even when the input mechanism is formal, the user may not always succeed in expressing his or her intention in the formal query language.

Information retrieval systems may use a variety of techniques to determine what information seems most relevant to a user's query. For some queries, the choice of technique is not particularly important: for example, if the user enters a query that is the exact title of a document, most techniques will retrieve that document as the most relevant result. For other queries, the choice of technique can be very significant, as different techniques may differ considerably in the results they return. Unfortunately, it is not always clear how to select the best technique for a particular query.

Over the past decade, the biomedical community has witnessed a surge in the volume of clinically relevant information converted to electronic form. The American Recovery and Reinvestment Act of 2009, with its mandate to digitize health records, ensures that this flow of information will continue to accelerate. Biomedical assay databases, both publicly-available and proprietary, boasting many gigabytes of data, have become commonplace. To harness the potential for these resources to impact clinical decision-making and therapeutic design, computational tools are needed for simultaneously retrieving source documents (electronic health records, assay data, etc.) related to a given medical concept simultaneously from a variety of such sources. While many institutions have developed proprietary in-house solutions to storing this data, there do not appear to be any standardized systems available for indexing and intelligently searching these databases based on medical concepts.

The National Library of Medicine's Unified Medical Language System (UMLS) (Bodenreider 2004) provides a hierarchical organization of a wide-ranging set of medical and biological concepts, and includes thesauri for mapping concepts across languages and dialects.

BRIEF SUMMARY

The subject matter of this disclosure is a scalable infrastructure for searching multiple disparate textual databases by mapping their contents onto a structured ontology, e.g., of medical concepts. This framework can be leveraged against any database where free-text attributes are used to describe the constituent records (for example, medical images might be associated with a short description).

The invention provides a framework for mapping both queries and source documents onto a structured ontology, such as the National Laboratory of Medicine's Unified Medical Language System (UMLS), to facilitate access to and integration of a wide variety of clinical data. In one embodiment, an information retrieval method begins in a first step by processing the free-text associated with various types of source data (e.g., clinical narrative from an electronic health record, a description of condition and treatment associated with a clinical assay, etc.) and mapping that text onto UMLS, which is a hierarchical representation of medical knowledge. A hierarchical structure of the UMLS ontology (an index) is then created such that references to the data records processed during the first step are stored at the vertices of this index. This data structure supports efficient lookups of records that match a concept of any of its subordinates. To that end, preferably a system that implements this approach provides a Simple Object Access Protocol (SOAP) interface (or the like) that allows Web 2.0 applications to query the index. Preferably, search queries are likewise mapped onto UMLS in the same manner so that the system can search for relevant documents in the structured space. In this manner, multiple synonymous terms that appear in both source documents and queries are mapped onto the same structured ontology.

According to another aspect of this disclosure, one or more spectral graph theory algorithms may be used to improve the quality of the query results by filtering false positives from the UMLS concept associations generated in the first step described above. The parameters for these algorithms may be obtained using expert-labeled training data, although this is not a requirement.

The above-described techniques enable the creation of a search tool for use to build portable applications that leverage the wide variety of data-rich resources that are becoming available, thus addressing one of the core challenges in personalized healthcare practice, identifying clinically distinct subgroups to which a particular patient belongs (Kohane 2009).

The foregoing has outlined some of the more pertinent features. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF REPRESENTATIVE EMBODIMENTS

Figure 1:
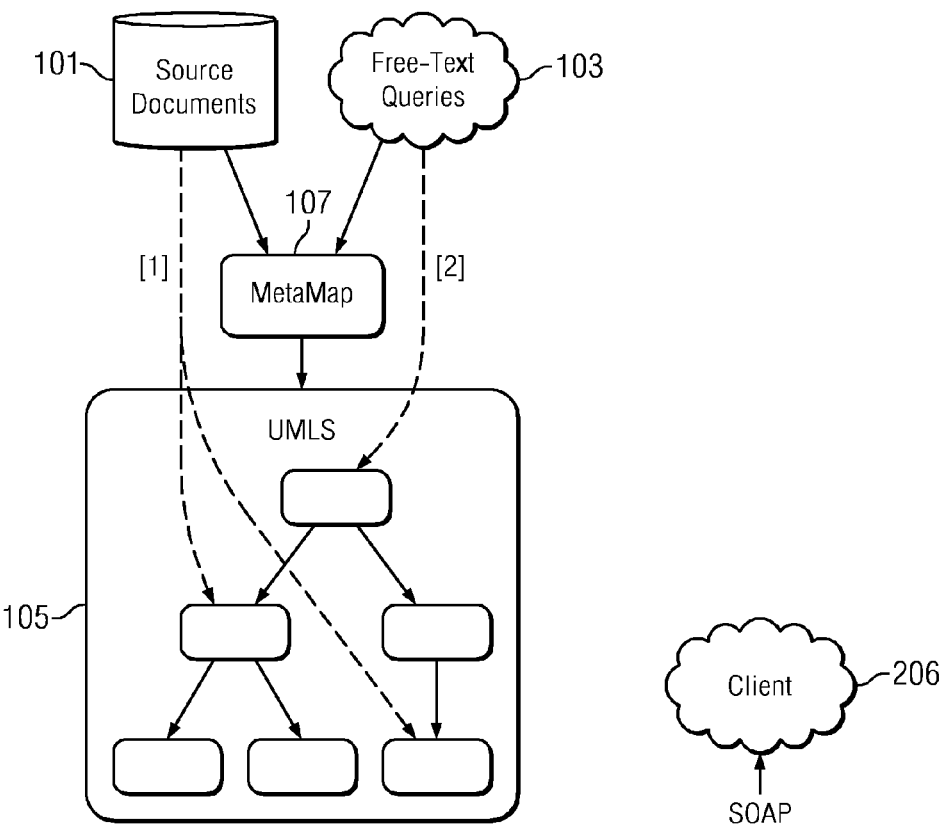
FIG. 1 is a schematic diagram of a natural language processing (NLP)-driven UMLS mapping system in which embodiments of this disclosure may be practiced.

There are major challenges arise when searching free-text medical literature as it appears in electronic medical records, medical reference volumes or other medical documents, namely, resolving synonyms and identifying conceptual relationships between medical terms. There are other challenges are addressed by building a system around the National Library of Medicine's Unified Medical Language System (UMLS) (Nadkarni, Chen et al. 2001). UMLS is an ontological organization of medical concepts, built from various thesauri, such as SNOMED (National Library of Medicine 2004), MeSH (National Library of Medicine 2008), and RxNorm (Liu, Ma et al. 2005). The techniques described below map both source documents and user queries into UMLS hierarchically structured space of medical concepts.

At a high level, the technique resolves multiple synonymous terms to unified concepts. As is well-known, multiple synonymous phrases are often used to describe one common medical or biological concept. For example, the terms "malignant neoplasm of the lung" and "lung carcinoma" both describe the same medical concept, but there is no agreement on which term should be used to describe the one underlying concept, a malignant cancerous growth appearing in the lung. To see where this becomes a challenge, consider searching a database for the phrase "lung carcinoma" where all of the constituent documents refer to "malignant neoplasm of the lung." Searching the database by simple string matching will fail to find the documents related to the query.

This disclosure addresses this problem by mapping the text content of each entity in the database to a controlled vocabulary, the UMLS. The UMLS consists of a series of "biomedical vocabularies developed by the US National Library of Medicine" (Nadkarni, Chen et al. 2001; Bodenreider 2004). The purpose of these expert-curated vocabularies is to provide a set of thesauri that map multiple synonymous phrases to a single unified concept. The collection of these mappings is called the UMLS Metathesaurus. MetaMap (Aronson 2001), a program that generates these thesaurus correspondences from free text, is available from the National Library of Medicine (NLM), and is the standard tool for such tasks. MetaMap matches simple syntactic noun phrases from an input text to UMLS concepts, effectively "standardizing" the text to a set of unique concepts. Alternative methods of mapping the text content to a controlled vocabulary may also be employed. One such example is regular expression matching the source text against a thesaurus that describes the synonymy between the vocabulary and terms that are likely to be used in free-text.

According to the techniques proposed herein, MetaMap or a similar mapping strategy is applied to database entities to alleviate the problem of resolving synonymous, but textually disparate phrases. Moreover, when the resulting database is later queried, the same standardization is applied to the input query as was used to transform the original source text, which allows the disclosed system to search for database entities matching the query in the structured space of standardized UMLS concepts rather than free-text. In addition, when a practitioner later wishes to perform large-scale data mining on such a database, the UMLS concepts associated with the database entities are treated as a discrete labeling thereof, without applying ad-hoc text searches to identify groups of related records.

The following provides a more detailed description of how to map documents and queries onto a given ontology (such as UMLS) of medical concepts. As is well-known, UMLS provides a hierarchical organization of the concepts that it contains. For example, the concepts "white blood cell abnormality," "thrombosis," "anemia," and "hemorrhage" are all among the descendants of the concept "hematological diseases" in the UMLS hierarchy. As described above, preferably a system that implements this invention processes free-text user queries with the same natural language processing (NLP)-driven UMLS mapping tool that is used to process the source documents, thus translating the query into the simpler task of identifying documents associated with the concept(s) to which it maps. FIG. 1 illustrates the preferred technique, wherein both the text from the source documents 101 and the free-text queries 103 get mapped to UMLS concepts 105 by an NLP-driven UMLS mapping tool 107, such as MetaMap. Querying for the parent concept [1] then returns all documents relating to child concepts, as they relate to the more specific concepts. Free-text queries [2] get mapped in a similar manner. Continuing the above example, any query that maps to the "hematological diseases" concept should return documents related to any one (or several) of these four subordinate concepts, even though the NLP mapping of the documents' source text may not have directly hit "hematological diseases." As can be seen, the expert knowledge encoded in this structure is exploiting by storing references to the source documents (e.g., medical records, diagnostic tests, medical literature) on top of the UMLS hierarchy (see below for additional details). This hierarchical index allows a search and retrieval system to efficiently traverse the ontology and retrieve records related to a particular concept and its subordinates.

As an extension or optimization, the system may efficiently aggregate documents that match arbitrarily complex logical combinations of UMLS concepts. In this alternative embodiment, a stack-based algorithm (such as Nyhoff 1999) may be used to evaluate infix set logic expressions. Here, the operands are set operators and the arguments are UMLS concepts. Conceptually, the algorithm works by replacing the stack entry for each UMLS concept in the expression with the set of database records that reference it, then proceeding with the logical evaluation as usual. This approach enables the user to perform free-text queries such as "anemia and cancer" or "lung cancer and metastasis but not smoking" against the library of documents.

Figure 2:
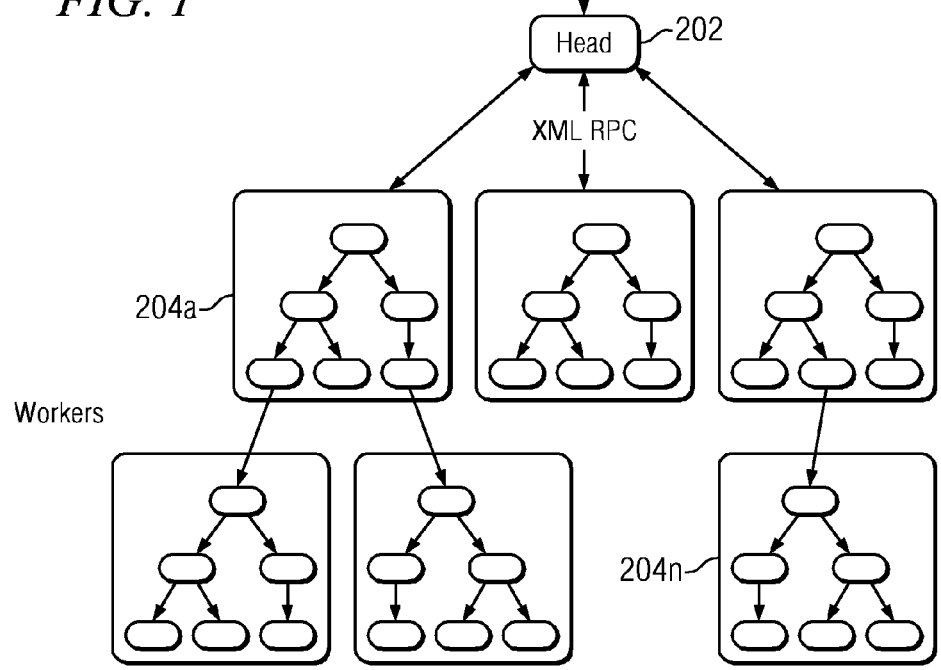
FIG. 2 is a distributed data processing infrastructure in which exemplary aspects of the illustrative embodiments may be implemented.

The following provides details of a machine-based (e.g., hardware and software) infrastructure for implementing the techniques described herein. Although traditional relational database systems (which index their records based on lexicographical ordering of key values, irrespective of conceptual relationships that exist between these keys) are typically regarded as more flexible than hierarchical databases, queries performed against the UMLS index require a traversal of the above-described UMLS topology. Thus, a hierarchically-structured database is preferable. Preferably, the database is structured such that each concept in the ontology is represented by a vertex in a tree (hierarchical) data structure, with references to the entities associated with each concept stored at the concept's respective vertex. This arrangement allows efficient implementation of the (e.g., recursive) graph-based algorithms used to search for documents related to particular concepts. As illustrated in FIG. 2, in this embodiment, SOAP-based queries are processed by a head node 202, which, in turn, requests that multiple worker nodes 204a-n perform the database search in parallel. Preferably, each of these worker nodes 204 is capable of searching a separate portion of the database. As illustrated, inter-nodal communications may be XML RPC (remote procedure call)-based, although this is not a limitation. Furthermore, it is not necessary for the complete tree structure to reside on a single worker node. Due to the hierarchical nature of the system, sub-trees can be split out to various worker nodes and queried either directly by the user, or by parent nodes querying their sub-tree(s). Results are then returned to the head node, or to the parent worker node that gave rise to the sub-query, aggregated, and returned to the requesting client (typically a Web 2.0-enabled Web browser) 206. This infrastructure enables a search and retrieval system that implements these techniques to scale to meet future needs by simply adding additional worker nodes. In addition, this system can be made fault tolerant in a mission-critical environment by replicating worker nodes or dynamically reassigning the responsibilities of a failed node.

As an optimization that improves responsiveness at the cost of additional data storage, the system pre-computes (for example, using a breadth-first-search algorithm) a list of all descendant concepts for each concept in the ontology. The task of retrieving all documents associated with a particular concept or any of its descendant concepts then is accomplished by retrieving the list of all descendant concepts for the requested concept and retrieving all document references for each descendant. This arrangement serves well for moderate throughput systems where updates (documents added to or removed from the database) need to appear in real time. Updates simply consist of modifying the record of concept/document associations for each concept referenced by the document being added or removed.

As an additional optimization, where higher throughput is desired, the above procedure may be pre-computed for each concept in the ontology. The resulting data structure (a hash table) provides a direct mapping from each concept to all documents that reference any of the concept's descendants in a single read operation (as opposed to iteratively retrieving documents for each descendant in real-time as described previously). Updates (adding and removing documents) are achieved by updating the hash table entries for each concept referenced by the document, as well as each referenced concept's descendants.

Various strategies can be employed to mitigate some of the increased storage requirements for the aforementioned optimizations. Instead of precomputing all of the descendant document associations for all concepts, a hybrid approach is possible. In this situation some concepts will have the complete mapping to all of their associated documents, while other concepts will query their descendant concepts for their concepts and aggregate the results. A further space-saving improvement is to store meta-documents instead of the individual document records. When returning the set of documents for a given concept, the system can then be configured to either return the meta-document, which will require a subsequent call to the system to unravel the contents, or configured to expand all meta-documents back such that a list of documents are returned.

The system may also pre-compute a mapping from each concept to all of its ancestors within the hierarchy. In this embodiment, this mapping then is used in conjunction with an auxiliary table that maps each document to a list of all associated concepts to provide a mapping between documents and all implied (via the ontology's hierarchy) concepts. This data structure may be used for data mining tasks (e.g., latent semantic indexing) where one wishes to learn patterns in the association of concepts and documents where the pattern can only be observed through the indirect associations implied by the hierarchy. For example, documents that reference specific subtypes of cancer may not appear similar to one another until they are aggregated at a higher level (for example, "cancer") in the UMLS ontology. As before, this mapping may be computed iteratively in real time, or it may be pre-computed to improve performance at the cost of additional storage requirements. The same space-saving strategies described above are applicable here.

In a representative embodiment, queries are submitted to the head node via a Simple Object Access Protocol (SOAP) API. This framework allows convenient access to the database from any third-party application. In addition, it can easily be secured to protect proprietary data. Simple Object Access Protocol (SOAP) is a lightweight XML based protocol commonly used for invoking Web Services and exchanging structured data and type information on the Web. Using SOAP, XML-based messages are exchanged over a computer network, normally using HTTP (Hypertext Transfer Protocol). Transport layer security mechanisms, such as HTTP over TLS (Transport Layer Security), may be used to secure messages between two adjacent SOAP nodes. Typically, a query is submitted using a Web browser that implements known Web 2.0 technologies. Thus, in a typical use scenario, an end user machine has a web browser or other rendering engine that is compatible with AJAX technologies (e.g., XHTML, XML, CSS, DOM, JSON, and the like). AJAX technologies include XHTML (Extensible HTML) and CSS (Cascading Style Sheets) for marking up and styling information, the use of DOM (Document Object Model) accessed with client-side scripting languages, the use of an XMLHttpRequest object (an API used by a scripting language) to transfer XML and other text data asynchronously to and from a server using HTTP), and use of XML or JSON (Javascript Object Notation, a lightweight data interchange format) as a format to transfer data between the server and the client.

One or more servers implement a search and retrieval system. That system comprises the one or more worker nodes described above. The persistent hierarchical database at each worker node may be implemented in Java, utilizing Oracle's BerkeleyDB JE package (as an example). This package is advantageous as it enables the search and retrieval system to easily serialize in-core data structures manipulated by the search algorithms without the communication overhead incurred when interacting with an out-of-core database service. In addition, the algorithms used to search the database may be more easily implemented by the programmer in Java (an imperative/object-oriented language) than they would be via SQL queries against a relational database. Preferably, worker nodes receive requests from the head node via XML-RPC, search their portion of the database, and return the results to the head node for aggregation. The use of Java in combination with SOAP and XML-RPC makes this software stack platform independent, easily portable, and requires no specialized cluster software. Of course, other hardware, software and database systems may be used.

A major shortcoming of natural language processing techniques to indexing biological and medical literature is the overabundance of false-positive results. To overcome such problems of over-sensitivity (false positive annotation), another aspect of this disclosure is the use of machine learning techniques to learn patterns of these incorrect UMLS annotations.

As is well-known, the field of spectral graph clustering encompasses methods for partitioning a (possibly weighted) graph such that the connectivity of the vertices within each partition (or cluster) is high, while connectivity between partitions is relatively low. Put another way, a particle traveling randomly between vertices (with probabilities proportional to the weights of the edges leaving each vertex) will tend to stay within each partition, and will tend to have a relatively hard time crossing low-weight edges between partitions. It is well known that the stationary distribution of this random walk is equal to the eigenvector with eigenvalue 1 of the transition matrix that describes the probability of moving between vertices.

To address the problem of false positives, according to another aspect of this invention, a matrix (such as a right stochastic matrix) is defined over a set of concepts in the database to approximate a random walk over the concepts according to their relative co-occurrence in literature. By using a natural language processing engine (e.g., the NLP engine used to annotate MedLine abstracts available from the NLM via the MedLine online resource), the frequency with which each concept appears proximal to every other concept in a large corpus of medical and biological literature can be estimated. Concept associations are then ranked for a given document by the random walk as described above on this co-occurrence matrix. Those concepts with a probability mass below a threshold after several steps are unlikely to be related to the other concepts, and thus are likely outliers.

The use of the truncated random walk requires the tuning of two parameters: the length of the walk, and the probability mass cutoff. The optimum values for these parameters may be determined by examining the sensitivity and specificity for a given probability cutoff at a given length of the random walk. Using a training set, for example, cross validation can be performed to robustly compute these values for various probability thresholds for a fixed number of steps up until the probability values converge. For example, to compute an n-fold cross-validation, a training set of documents is randomly partitioned into n equal parts, with (n−1) of these parts constituting the training set while the remaining one is used as the test set. By repeating the sensitivity and specificity computation for each part, one can compute n sensitivity and specificity values that can be averaged for a robust measure.

The search and retrieval applications that use the above-described framework may be used by hospitals, medical schools, biology labs, and so on, and the users of such systems and applications can be viewed as semi-experts. Users thus can be allowed to "vote" on how much they like a particular search result. If there are a sufficient number of users that deem a given record to be incorrect the annotation can either be removed automatically or the record can be put up to be reviewed by an expert. Conversely, if there is a result that is a very good match, it can be up-weighted causing it to appear earlier in the search results. In the simplest case, this can be modeled with a beta distribution such that $\alpha$ represents the number of positive votes and $\beta$ the number of negative votes for each UMLS concept associated with a given document. Using cross-validation on the validated set of documents the thresholds necessary for considering a UMLS concept associated with a document as incorrect or correct can be discovered.

Figure 3:
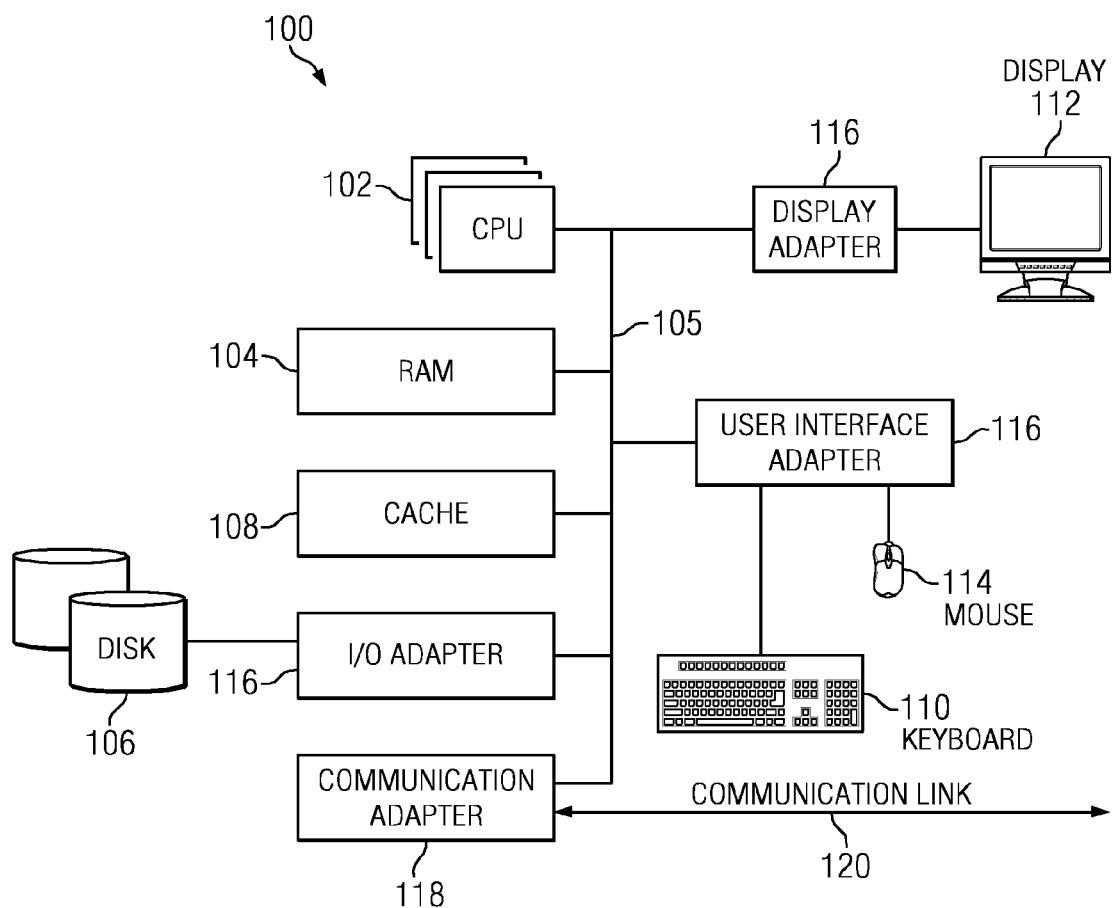
FIG. 3 is an information retrieval system for use to practice the subject matter described herein.

FIG. 3 is a simplified block diagram of a representative information retrieval system in which the subject matter described herein may be implemented and comprises a data processing system. As seen in FIG. 1, a data processing system 100 suitable for storing and/or executing program code will include at least one processor 102 coupled directly or indirectly to memory elements through a system bus 105. The memory elements can include local memory 104 employed during actual execution of the program code, bulk storage 106, and cache memories 108 that provide temporary storage of at least some program code to reduce the number of times code must be retrieved from bulk storage during execution. Input/output or I/O devices (including but not limited to keyboards 110, displays 112, pointing devices 114, etc.) can be coupled to the system either directly or through intervening I/O controllers 116. Network adapters 118 may also be coupled to the system to enable the data processing system to become coupled to other data processing systems or devices through intervening private or public networks 120.

The framework described above allows UMLS to become the common language to connect a wide variety of clinically relevant databases. The invention, however, is not limited to the UMLS ontology. As one of ordinary skill in the pertinent art will appreciate, applications may make use of the framework to index and provide users the ability to retrieve various types of clinical and biological data. Indeed, the framework may be leveraged against any database where free-text attributes are used to describe the constituent records.

As examples, the framework may be used to support search application for the publicly-available gene expression (microarray) data from NCBI's Gene Expression Omnibus (GEO) resource (Edgar, Domrachev et al. 2002) and from electronic health records (EHRs). These are merely representative applications. GEO is a central repository where researchers can store, share and explore high-throughput transcription data generated in laboratories throughout the world. Each expression sample submitted to the repository represents a unique, noisy snapshot of the transcriptional state space of the biological sample from which the sample was hybridized and is associated with several pieces of free-text metadata provided by the original submitter describing the phenotype (e.g., cell type, treatment condition, disease state). Considered en masse, this data may encode conserved, statistically significant signals describing the transcriptional programs underlying many biological processes. For example, this system could be used to find a gene's specificity as a biomarker if it was found to be up- or down-regulated in a specific phenotypic condition by examining its behavior in other phenotypic conditions. The large volume of publicly-available data in such a resource may be processed according to the techniques described above to facilitate large-scale automated analysis and data mining.

An application for electronic health records may use the same framework. Current medical record software appear to index their records on some basic patient identifier(s) (name, date of birth, social security number, etc.) and are optimized for searching based on those identifiers. This clearly is not ideal for finding the set of all patients with a given phenotypic condition for a clinical study. By using MetaMap to annotate the various fields in each record (doctor's notes, diagnoses, etc.), the above-described technique maps each record to the set of UMLS concepts that describe its contents. A user of the application based on the framework can then search for records based on any medical concept found in UMLS. For example, one can query for skin rashes and cancer to find patients for a study on paraneoplastic processes. Since the UMLS concepts reside in an ontology, even if a patient record never explicitly mentions the general term "cancer," but rather a more specific type of cancer, the system would correctly include this patient's record in the search results.

The techniques described above have broad applicability in both clinical and biomedical research communities. The framework for making medical text machine-intelligible may be extended and used for any electronic medical record system. The utility of the framework will increase over time as the volume of medical information converted to electronic form grows. Rather than simply providing persistent storage of such documents, this disclosure provides for a unified, standardized search and retrieval tool that will allow the practitioner of medical, biological, or information sciences the ability to query a wide variety of document sources, and navigate the results in an intuitive and meaningful way. Additional applications of such data include identification of populations for recruitment and sample acquisition, and observational studies married to sophisticated time-series analysis for, among other purposes, pharmacovigilance (PV) and biosurveillance.

Generalizing, the framework and the techniques described herein are not limited for use with respect to clinical and biological data. One of ordinary skill will appreciate that the techniques have broad applicability for search and retrieval applications and systems, regardless of the field of use. These fields include, without limitation, conventional Web search, semantic Web search, and the like. As an example, the W3C's Resource Description Framework (RDF) can be modeled using this framework. The Uniform Resource Identifiers (URIs) become the concepts and the relationships between them are edges that associate the various concepts. The application can then answer complex queries based on these URIs.

The subject matter described herein can take the form of an entirely hardware embodiment, an entirely software embodiment, or an embodiment containing both hardware and software elements. One preferred embodiment takes the form of software executing in one or more server machines connected by a network. The invention (or portions thereof) may take the form of a computer program product accessible from a computer-usable or computer-readable medium providing program code for use by or in connection with a computer or any instruction execution system. A computer-usable or computer readable medium can be any device or apparatus that can include, store or communicate the program for use by or in connection with the instruction execution system, apparatus, or device. The medium can be an electronic, magnetic, optical, or the like. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

The description of the disclosed subject matter has been presented for purposes of illustration and description, and is not intended to be exhaustive or limited to the form disclosed. Many modifications and variations will be apparent to those of ordinary skill in the art. The embodiment was chosen and described to best explain the inventive principles, a practical application, and to enable others of ordinary skill in the art to understand the various embodiments.

The techniques described herein may be implemented in or in conjunction with various server-side architectures including simple n-tier architectures, web portals, hosted or cloud-based systems, and the like.

While given components of the system have been described separately, one of ordinary skill will appreciate that some of the functions may be combined or shared in given instructions, program sequences, code portions, and the like.

The techniques described above can be used with any structured ontology, which is a formal representation of knowledge by a set of concepts within a domain, and the relationships between those concepts. It is used to reason about the properties of that domain, and it may also be used to describe the domain.

The techniques described herein are not limited to any particular information retrieval system or collection of documents. Also, the terms "information retrieval" and "documents" should be broadly construed. As is well-known, information retrieval systems aim to solve the problems associated with searching for information in a collection of documents. Generally, they comprise technologies for searching for documents, as well as searching for metadata that describes documents. Typically, documents are discrete text files that may also be associated with metadata, such as a name, author, and date of creation. However, documents may also represent other addressable and selectable media, including without loss of generality non-textual data, such as sound and visual recordings, database records, and composite entities such as might be described using HTML and XML encoding. Similarly, although a "set of documents" may describe the entire collection of documents available to the information retrieval system, it may be applied equally well to a subset of the whole; for example, all documents permitted to be accessed within a currently active security, privacy or confidentiality regime, or a collection of documents previously selected by the user to be manipulated by the information retrieval system. Thus, both individual documents and collections of documents may take many forms, including file systems, relational databases, hypertext collections (such as the World Wide Web), or the like.

Having described our invention, what we now claim is as follows:

1. Apparatus for information processing, comprising:
a processor; and
computer memory storing computer program instructions that when executed by the processor perform a method comprising:
normalizing, using a natural language processing (NLP) mapping, text contents of a set of documents onto a structured ontology, the text contents in the set of documents representing at least one concept in the structured ontology having a set of subordinate concepts that are described by synonymous, but textually disparate phrases;
modeling the structured ontology as a hierarchical data structure;
normalizing a search query using the NLP mapping used to normalize the text contents of the set of documents; and
processing the normalized search query against the hierarchical data structure in lieu of the search query to identify documents associated with the at least one concept, the processing of the normalized search query associated with the concept also returning results associated with the subordinate concepts.

2. The apparatus as described in claim 1 wherein the structured ontology represents a hierarchical representation of medical knowledge.

3. The apparatus as described in claim 2 wherein the hierarchical representation is Unified Medical Language System (UMLS).

4. The apparatus as described in claim 1 wherein the hierarchical data structure is structured for a traversal operation.

5. The apparatus as described in claim 1 wherein the normalizing step maps text contents of the set of documents to a controlled vocabulary.

6. The apparatus as described in claim 1 wherein the structured ontology is stored in a hierarchical database.

7. The apparatus as described in claim 6 wherein a particular concept in the structured ontology is represented in the hierarchical database by a vertex, and wherein a reference to an entity associated with the particular concept is stored at the vertex.

8. The apparatus as described in claim 7 wherein the step of processing the search query uses a recursive graph-based algorithm.

9. The apparatus as described in claim 6 wherein the step of processing the search query comprises search first and second portions of the hierarchical database concurrently.

10. The apparatus as described in claim 9 wherein the first and second portions of the hierarchical database are associated with first and second machines.

11. The apparatus as described in claim 10 wherein the first and second machines are located remotely from one another.

12. The apparatus as described in claim 1 wherein the method further includes the step of pre-computing a data structure that maps from each concept in the structured ontology to all documents in the set of documents that reference any of the concept's descendents.

13. The apparatus as described in claim 1 wherein the method further includes pre-computing a mapping from each concept in the structured ontology to all of its ancestors within the hierarchical data structure.

14. The apparatus as described in claim 13 wherein the method further includes using the pre-computed mapping with a data structure that maps each document in the set of documents to a list of associated concepts in the structured ontology.

15. Apparatus for information processing, comprising:
a hardware processor; and
computer memory storing computer program instructions, the computer program instructions comprising:
program code to normalize text contents of a set of documents onto a structured ontology;
program code to process the structured ontology to reduce false positives by ranking concept associations for a given document using a random walk algorithm;
program code to model the structured ontology as a hierarchical data structure;
program code to map a search query onto the structured ontology; and
program code to process the search query against the hierarchical data structure.

16. Apparatus for information processing, comprising:
a hardware processor; and
computer memory storing computer program instructions, the computer program instructions comprising:
program code to normalize text contents of a set of documents onto a structured ontology using a natural language processing (NLP) mapping;
program code to model the structured ontology as a hierarchical data structure;
program code to normalize a search query into a normalized search query using the NLP mapping;
program code to pre-compute a list of descendent concepts for a particular concept in the structured ontology; and
program code to process the normalized search query against the hierarchical data structure in lieu of the search query, wherein, as the normalized search query is processed, documents from the set of documents for each descendent are iteratively retrieved.

* * * * *